May 2, 1972 H. HOLTKAMP Plant Pat. 3,146
AFRICAN VIOLET
Original Filed Oct. 7, 1968
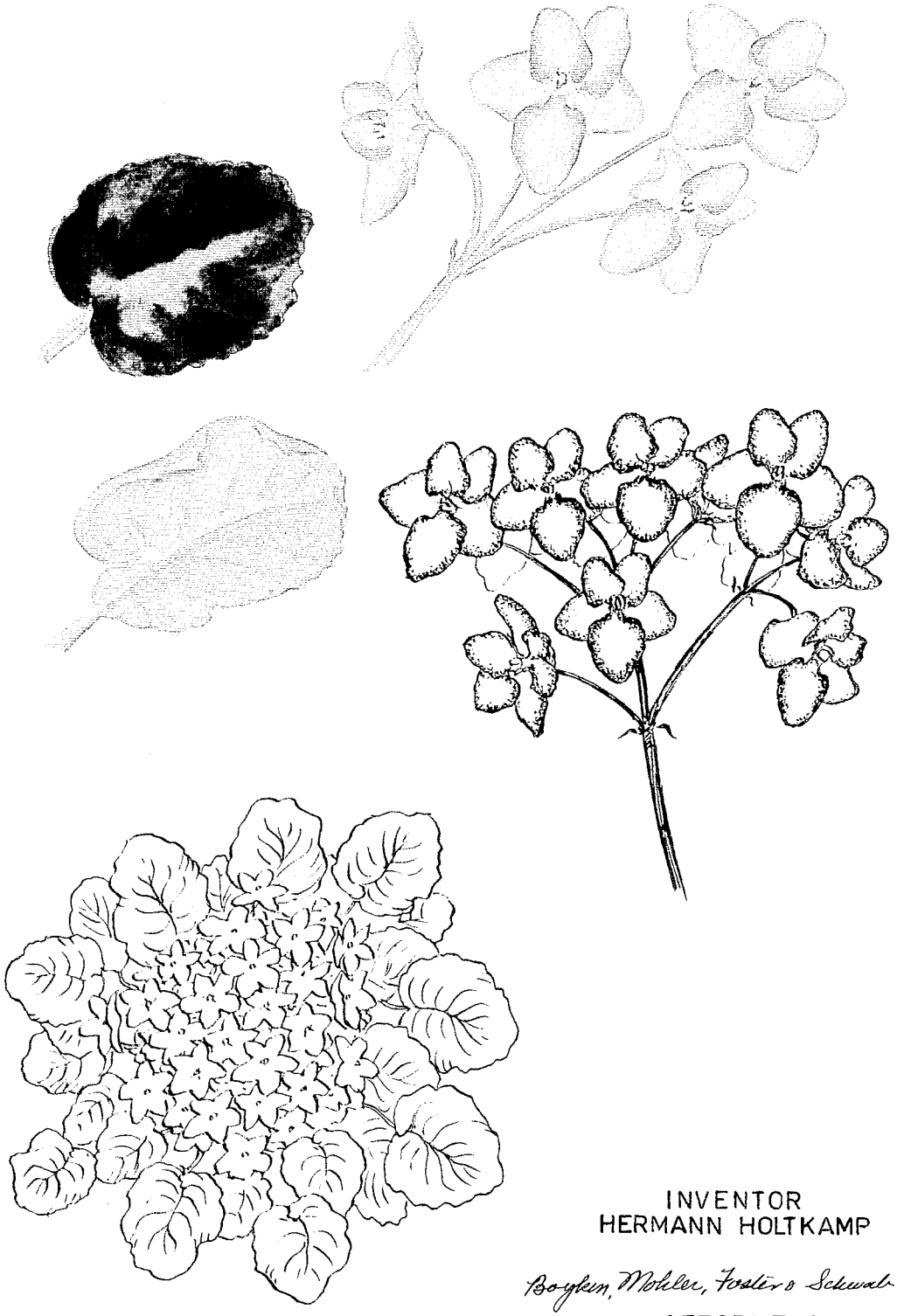
INVENTOR
HERMANN HOLTKAMP
Boyken, Mohler, Foster & Schwab
ATTORNEYS

United States Patent Office

Plant Pat. 3,146
Patented May 2, 1972

3,146

AFRICAN VIOLET

Hermann Holtkamp, Werther Strasse 5–7, Postfach 19, 4243 Isselburg, Germany

Original application Oct. 7, 1968, Ser. No. 765,700, now Patent No. 3,053. Divided and this application Sept. 14, 1970, Ser. No. 72,245

Int. Cl. A01h *5/00*

U.S. Cl. Plt.—69 1 Claim

ABSTRACT OF THE DISCLOSURE

A hybrid violet of a descendant of a cross between the *Saintpaulia ionantha* and *Saintpaulia shumensis* species which has permanent new characteristics including strength of stem, fast and vigorous growth, profuse flowering, uniform bouquet, prolonged blooming period, resistance to disease, reliability in initiating new plantlets, retention of flowers past maturity on their respective stems, reliability in new plants retaining characteristics of the parent and pronounced uniformity throughout the life cycle.

BRIEF SUMMARY OF THE INVENTION

This is a division of application Ser. No. 765,700, filed Oct. 7, 1968.

To obtain the present violet with the above mentioned permanent new characteristics, the inventor has executed numerous experiments, the first of which involved the selection and cross-pollenation of one of the parent plants, the *Saintpaulia ionantha*. The male parent in that series of experiments was the Saintpaulia species "Rokoko-Rhapsodie" and the female parents were chosen initially for their particular color characteristics such as the Saintpaulia species "Rosa-Rhapsodie" and Saintpaulia species "Rhapsodie in Blau" and others.

The pollenation of the parent plants was direct with the help of a fine dust brush. The seed pods of the pollenated plants developed normally and the seeds ripened well. The acquired seeds were used as the generic basis for initiating further experimental series. About 30,000 seedlings were cultivated, and from these, approximately 25 seedlings were selected by very rigid standards for further propagation.

The phenotype of the derivative plant as compared with the appearance of the parent plants evidenced substantial change. Propagation of these plants and the refinement out of limited selected plants continued and tests were conducted for the development of permanent characteristics of disease resistance, early blooming and vigorous growth. After several series of experiments and refinements, a single plant was selected and further tested to ascertain that the new characteristics were permanent.

The descendants of this plant were completely the same in appearance as the parent plant. The permanent qualities and characteristics included fast and vigorous growth, profuse blooming, a strong stem by African violet standards and resistance to disease.

The plant of the new variety, hereinafter described more in detail, is a hybrid of a descendant of a cross between the above-described improved *Saintpaulia ionantha* and the wild *Saintpaulia shumensis*, in which new variety the characteristics above-described for the aforesaid *Saintpaulia ionantha* are retained, but are materially improved, together with the feature of a compact, large, central flower head in the mature plants, within and above a wreath of leaves. The flowers in the present new variety are white with a bluish edge, and the variety is designated "Rhapsodie" Gigi.

Other desirable characteristics of the plant may appear in the drawings and description.

DESCRIPTION OF DRAWINGS

The upper illustrations show, in full color, a cluster of flowers on one of the petioles with flowers thereon, and opposite sides of one of the leaves; and below is shown in pen and ink one of the stems with flowers thereon, and a top plan view, in reduced size, of a plant illustrating a flower head and wreath of leaves therearound.

DETAILED DESCRIPTION

The botanical description of the plant of the present variety is as follows, the colors being later specifically described in tabular form; "Dictionary of Color" by Maerz and Paul.

*"Rhapsodie" Gigi, type 9/12*

Male parent: "Rhapsodie Blue-White", type 8/17.
Female parent: "Rhapsodie Blue," type 8/31.

*Plants.*—5 to 6½ inches tall.

*Leaves.*—Borne in rosette arrangement from 9 to 11 inches in diameter. Shape—oval, edges slightly scolloped. Length—2½ to 3½ inches. Width—2½ to 3 inches. Color—upper side medium green. Under side light green. Petiole—light green.

*Flowers.*—Borne profusely in a central flower head, forming a compact upright bouquet above foliage, 5½ to 6½ inches in diameter.

*Individual flowers.*—Quinquepartite, bilaterally symmetrical. (Petals have generally arrow-head outlined.) Size—½ to 2 inches in diameter. Color—white with blue edge. Calyx—quinquepartite. Peduncles—multiflorous up to 5 inches long, borne on long shafted cymes, with 6 to 14 flowers.

*Reproductive organs.*—Stamens—two fructified. Anthers—light yellow. Ovary—pilous. Seed capsule—does not push through.

*Roots.*—Well developed root system, white when young and active, turning to brownish color on older plants.

The color designations, according to "Dictionary of Color" by Maerz and Paul are as follows:

| | Plate | Letter | No. |
|---|---|---|---|
| Body of leaf: | | | |
| Upper side—Dark green | 24 | J | 4 |
| Under side—Light green | 18 | B | 6 |
| Petiole—Light green | 18 | J | 7 |
| Main body of flower—White blue marginal portion | 42 | J | 11 |
| Anthers—Light yellow | 9 | L | 1 |

GENERAL OBSERVATIONS

The following permanent characteristics are in all plants developed by me from the original cross pollenation of *Saintpaulia ionantha* with the wild *Saintpaulia shumensis* as hereinbefore described, including the present "Rhapsodie" Gigi above described in detail, and hereinafter claimed.

Strength of stem.—In the present new variety the stem is markedly stronger than heretofore and is capable of supporting approximately twenty-five to thirty blooms per stem when the plant is at full maturity.

Fast and vigorous growth.—The plants of the present variety will show first flowers approximately 6 weeks after potting and can be brought again to bloom in approximately 4 to 5-week cycles. In terms of commercial production, it becomes extremely important inasmuch as the time for bringing a plant to full maturity will be shortened by as much as two weeks for each blooming cycle reducing the total time for bringing the plant to commercial maturity by approximately two and one-half months. It will be appreciated that this is of significant importance in terms of utilization of space and crop productivity on a commercial basis. Under normal growing conditions, the plant will roughly double in size with each flowering.

Profuse flowering.—In the plant of this new variety the number of blossoms per stem, as well as the number of stems, increases with each flowering. Approximately six blooms per stem can be expected at first flowering, approximately double that number with the second flowering. At full maturity, each stem may have approximately twenty-five to thirty blooms and each stem has the strength to support that number.

Uniform bouquet.—In the present plant, the blossoms uniformly open above the leaves. The stems come up through the middle of the plant and the flowers form a well defined, attractive and compact crown characterized by shorter petioles and which crown is substantially hemispherical. The bouquet formed by the opened blossoms above the leaves is well centered and is almost completely uninterrupted by the intrusion of leaves and this characteristic is found uniformly throughout the series.

Prolonged blooming period.—When the flowers of the present variety are not cut back to force shorter blooming cycles, the blooming period is markedly longer than heretofore. Even as the flowers ripen past maturity, the appearance of the prolonged blooming period is maintained inasmuch as the flowers will not drop from the stems. There are no naked flower stems protruding from the bouquet inasmuch as the flower will remain on the stem until it withers.

Resistance to disease.—Resistance to disease in the present plant variety is notably improved over prior African violets. Of primary concern to breeders and growers of African violets in the past has been soft rot, mildew and botrytis which are caused by flowers opening beneath the leaves of the plant and primarily by early dropping of the flowers from their respective stems into the stem structure and pot as the flower ripens. These diseases can lead to complete decay of the plant. In the present variety, these problems are overcome inasmuch as the flowers uniformly open above the leaves of the plant and the ripened flowers will not drop from the flower stems. Each flower stays on the stem until it withers and will not drop into the moist soil at the top of the pot where it could lead to the above diseases. In the past the effective remedy for the above diseases was to promptly remove flowers as they fell. The benefit of less care and attention is especially appreciated in a commercial operation. In the present variety, the leaf cuttings will initiate a percentage of plantlets in the high 90 percent range and they will come up at substantially the same time which is uniformly earlier than heretofore, and the initiated plantlets are also of uniformly higher quality.

Inherited characteristics.—The new plants will uniformly carry the characteristics of the parent plant. These characteristics include color and shading of flower, color and shape of leaf, uniform and vigorous growth characteristics, and the other new and permanent characteristics of the present variety above enumerated.

Pronounced uniformity.—Perhaps the most important characteristic of the present variety of African violet is that of uniformity. Uniformity and reliability are found at every point in the growing of this variety.

In plants initiated at one time from leaf cuttings virtually all plantlets uniformly come up at the same time and bloom at the same time following the planting.

Given the proper growing room, the leaves of the plants will describe a uniform foundation and backdrop for the opening flowers. As the plant matures toward first blooming, substantially all of the plants of a given flat will bloom at the same time. The flower stems protrude through the leaves and the flowers will open above the backdrop of leaves and will be uniformly centered in that backdrop forming a compact, single crown or bouquet of blossoms. After cutback, the plants will uniformly bloom again in four to five weeks, again producing a well defined, full bouquet roughly double in size from that of the last blooming.

Since the plant roughly doubles in size with each flowering, it becomes commercially impractical to keep them beyond approximately one year because of the storage problems. Plants of the present variety approximately twelve months old and grown under normal conditions, will acquire a size of approximately eighteen to twenty inches in diameter and will yield approximately five hundred to six hundred individual flowers. Because of the uniformly high quality of the present variety, almost all of the plants are considered good for show purposes.

While there may be minor variations in the leaf size and shape, and in the shape of the flowers, which are common to African violets, the other characteristics hereinbefore described are constant. Of particular importance are: (1) the uniformly large, compact bouquet or flower head in each plant of approximately five and one-half to six and one-half inches in diameter at the second blooming, supported centrally of and above a wreath of dark green leaves; (2) approximately six to eight flowers per stem at first blooming and approximately double that number at second blooming, and twenty-five to thirty flowers per stem at full maturity; (3) substantially simultaneous and early blooming of the flowers on the stems of each plant at each blooming, and substantially simultaneous blooming of all plants started from leaf cuttings at the same time under the same conditions and maintained under the same conditions at each blooming; (4) a plant having the foregoing features in which the flowers are white and the petals have bluish marginal portions and which in subsequent propagations are of substantially the same color.

I claim:

1. A distinct variety of African violets substantially as herein shown and described, characterized as to novelty by a habit of bearing a large, solid, flower head, which head is from five and one-half to six and one-half inches in diameter at second blooming with approximately six to eight stems in each plant at first blooming, supporting the flowers of each flower head being above a wreath of dark green leaves on each plant surrounding the flower head and supporting approximately six to eight blooms on each stem at first blooming and double that number at second blooming, and approximately twenty-five to approximately thirty flowers per stem at full maturity, a long blooming period, and said plants being further characterized by substantially simultaneous early blooming of the flowers on the stems of each plant at each blooming, and substantially simultaneous blooming of all plants started from leaf cuttings at the same time under the same conditions and having the same treatment, and a distinctive and attractive white flower having petals with bluish marginal portions, and which flowers do not drop from the stems after withering, thereby avoiding damage and destruction due to mildew and botrytis from fallen blossoms.

No references cited.

ROBERT E. BAGWILL, Primary Examiner